United States Patent

Wassenaar

(10) Patent No.: US 9,163,100 B2
(45) Date of Patent: Oct. 20, 2015

(54) CATALYSTS FOR PREPARING ULTRA HIGH MOLECULAR WEIGHT POLYETHYLENE (UHMWPE)

(75) Inventor: Jeroen Wassenaar, Huizingen (BE)

(73) Assignee: TOTAL RESEARCH & TECHNOLOGY FELUY, Seneffe (Feluy) (BE)

( * ) Notice: Subject to any disclaimer, the term of this patent is extended or adjusted under 35 U.S.C. 154(b) by 0 days.

(21) Appl. No.: 14/236,984

(22) PCT Filed: Aug. 2, 2012

(86) PCT No.: PCT/EP2012/065172
§ 371 (c)(1),
(2), (4) Date: Apr. 15, 2014

(87) PCT Pub. No.: WO2013/020896
PCT Pub. Date: Feb. 14, 2013

(65) Prior Publication Data
US 2014/0309385 A1    Oct. 16, 2014

(30) Foreign Application Priority Data

Aug. 5, 2011   (EP) .................................. 11176732

(51) Int. Cl.
| | |
|---|---|
| C08F 4/64 | (2006.01) |
| C08F 4/76 | (2006.01) |
| C07F 7/00 | (2006.01) |
| B01J 31/18 | (2006.01) |
| C08F 110/02 | (2006.01) |
| C08F 4/60 | (2006.01) |

(52) U.S. Cl.
CPC ............ *C08F 110/02* (2013.01); *C08F 4/60048* (2013.01); *B01J 31/18* (2013.01); *C07F 7/006* (2013.01)

(58) Field of Classification Search
CPC ........ C08F 7/00; C08F 4/60048; C08F 10/02; C08F 2500/01; C08F 2500/03; C08F 2500/17
USPC .......................................... 526/172, 161, 352
See application file for complete search history.

(56) References Cited

U.S. PATENT DOCUMENTS

| | | | |
|---|---|---|---|
| 6,635,728 B2 | 10/2003 | Liu | |
| 7,091,272 B2 | 8/2006 | Liu | |
| 7,951,743 B2 | 5/2011 | Wang | |
| 8,492,493 B2 * | 7/2013 | Carpentier et al. | ........... 526/172 |

(Continued)

FOREIGN PATENT DOCUMENTS

| | | |
|---|---|---|
| CN | 101412763 A | 4/2009 |
| CN | 102015740 A | 4/2011 |

(Continued)

OTHER PUBLICATIONS

Howard et al. Dalton Trans., 2009, 8667-8682.*

(Continued)

*Primary Examiner* — Rip A Lee (57) ABSTRACT

Group 4 transition metal complexes of bidentate iminonaphthol pro-ligands can be used as catalysts to polymerise olefins, such as ethylene. Group 4 transition metal complexes of bidentate iminonaphthol pro-ligands can have a single-site nature, allowing the catalysts to be used to prepare ultra high molecular weight polyethylene having a narrow molecular weight distribution.

22 Claims, 1 Drawing Sheet

(56) References Cited

U.S. PATENT DOCUMENTS

2009/0163682 A1* 6/2009 Miranda et al. ............... 526/160
2010/0056737 A1 3/2010 Dickner et al.

FOREIGN PATENT DOCUMENTS

| EP | 0277004 A1 | 8/1988 | | |
|----|------------|--------|---|---|
| EP | 0427696 A2 | 5/1991 | | |
| EP | 1555272 A1 | 7/2005 | | |
| EP | 2113507 A1 | 11/2009 | | |
| WO | 2009/133026 A1 | 11/2009 | | |
| WO | WO 2009/133026 A1 * | 11/2009 | ............. | C07F 11/00 |
| WO | 2010/139720 A1 | 12/2010 | | |
| WO | 2011/089017 A1 | 7/2011 | | |

OTHER PUBLICATIONS

Makio, H. et al.: "FI Catalysts: A New Family of High Performance Catalysts for Olefin Polymerization", Advanced Synthesis & Catalysis, Wiley-VCH Verlag, Weinheim, DE, vol. 344, No. 5, Jan. 1, 2002, pp. 477-493, XP001540006.

Jones, R. L. et al., "Catalysts for UHMWPE and UHMWPE-copolymers", Inorganica Chimica Acta, Elsevier BV, NL, vol. 364, No. 1, Dec. 15, 2010, pp. 275-281, XP027545513.

Matsui et al., "FI Catalysts: super active new ethylene polymerization catalysts", Mitsui Chemicals Inc., Catalysis Today, vol. 66, Issue 1, Mar. 15, 2001, pp. 63-73.

Makio et al., "FI Catalysts for Olefin Polymerization—A Comprehensive Treatment", Chemical Reviews, 2011, vol. 111, pp. 2363-2449.

Weiser et al., "The synthesis and X-ray structure of a phenoxyimine catalyst tailored for living olefin polymerisation and the synthesis of ultra-high molecular weight polyethylene and atactic polypropylene", Journal of Organometallic Chemistry, vol. 691, 2006, pp. 2945-2952.

Rastogi et al., "Unprecedented High-Modulus High-Strength Tapes and Films of Ultrahigh Molecular Weight Polyethylene via Solvent-Free Route", Macromolecules, vol. 44, 2001, pp. 5558-5568.

Marvin Charton, "Steric Effects. I. Esterification and Acid-Catalyzed Hydrolysis of Esters", Journal of the American Chemical Society, 97:6, Mar. 19, 1975, pp. 1552-1556.

"Chapter 9: Effects of Structure and Medium on Reactivity", March's Advanced Organic Chemistry: Reactions, Mechanisms, and Structure, 6th Edition, John Wiley & Sons, Inc., 2007, pp. 395-416.

International Search Report issued in PCT/EP2012/065172 mailed on Oct. 17, 2012 (3 pages).

Makoto Mitani, et al., "Fluorine- and Trimethylsilyl-Containing Phenoxy-Imine Ti Complex for Highly Syndiotactic Living Polypropylenes with Extremely High Melting Temperatures", J.Am. Chem.Soc., vol. 124, pp. 7888-7889, published on Jun. 18, 2002.

Chinese Office Action issued in Application No. 201280048391.3, dated Jul. 3, 2015, 19 pages.

J. Saito, et al., "Living Polymerization of Ethylene with a Titanium Complex Containing Two Phenoxy-Imine Chelate Ligands"; Angew. Chem., Int. Ed., vol. 40, No. 15; pp. 2918-2920; 2001.

* cited by examiner

CATALYSTS FOR PREPARING ULTRA HIGH MOLECULAR WEIGHT POLYETHYLENE (UHMWPE)

CROSS-REFERENCE TO RELATED APPLICATIONS

This application claims the benefit of PCT/EP2012/065172, filed on Aug. 2, 2012, which claims priority from EP 11176732.3, filed on Aug. 5, 2011.

FIELD OF THE INVENTION

The invention relates to a single-site catalyst suitable for the preparation of ultra high molecular weight polyethylene (UHMWPE). The invention further relates to a process for preparing said UHMWPE, to the UHMWPE obtained from said process the use of said UHMWPE in various applications e.g. biomedical devices, ballistic protection, fishing and sailing ropes.

BACKGROUND

UHMWPE has a molecular weight of at least 1,000,000 Da, which is 10 to 100 times greater than the molecular weight of high-density polyethylene (HDPE). UHMWPE offers major advantages in increased impact resistance, tensile strength, abrasion resistance, and stress-crack resistance. UHMWPE can be produced by Ziegler polymerization. The process requires exceptionally pure ethylene and other raw materials. Like conventional HDPE, UHMWPE made by Ziegler polymerization has a broad molecular weight distribution Mw/Mn (Mw is the weight average molecular weight, Mn is the number average molecular weight) of within the range of 5 to 20.

However, UHMWPE with a narrow molecular weight distribution Mw/Mn of less than 5 have improved mechanical properties. Newly developed metallocene and single-site catalysts advantageously provide polyethylene and other polyolefins with very narrow molecular weight distribution (Mw/Mn from 1 to 5). The narrow molecular weight distribution results in reduced low molecular weight species and higher Mn which further improves abrasion resistance. These new catalysts also significantly enhance incorporation of long-chain α-olefin comonomers into polyethylene, and therefore reduce its density. Unfortunately, however, these catalysts produce polyethylene having a lower molecular weight than that made with Ziegler-Natta catalysts. It is extremely difficult to produce UHMWPE with conventional metallocene or single-site catalysts.

However, some allege to have obtained UHMWPE with various single-site catalysts.

U.S. Pat. No. 7,951,743 discloses an ultra-high molecular weight, linear low density polyethylene obtained with a catalyst system that comprises a bridged indenoindolyl transition metal complex, a non-bridged indenoindolyl transition metal complex, an alumoxane activator and a boron-containing activator. The ultra-high molecular weight, linear low density polyethylene has a Mw greater than 1,000,000 and a density less than 0.940 g/cm$^3$.

U.S. Pat. No. 7,091,272 B2 discloses an olefin polymerization process in the presence of a clay, an activator, and a transition metal complex that has at least one pyridine moiety-containing ligand. The presence of clay increases the catalyst activity. The process is suitable for making ultra-high molecular weight polyethylenes (UHMWPE).

U.S. Pat. No. 6,635,728 B2 discloses an ethylene polymerization process with a supported quinolinoxy-containing single-site catalyst in the presence of a non-alumoxane activator, but in the absence of an α-olefin comonomer, an aromatic solvent, and hydrogen to produce UHMWPE.

US 2010/0056737 A1 discloses a process of manufacturing high, very high, and ultra high molecular weight polymers comprising predominantly ethylene monomers. Ethylene is reacted in the presence of a catalyst system to produce a polymer having a viscosimetrically-determined molecular weight of at least 0.7×10$^6$ g/mol. The catalyst system generally includes a bridged metallocene catalyst compound, optionally with a cocatalyst. The catalyst is characterized by a zirconium dichloride central functionality and a dimethyl silandiyl bridge between five-membered rings of indenyl groups. Both rings of the metallocene compound are substituted at the 2-position with respect to the dimethyl silandiyl bridge with a $C_1$-$C_{20}$ carbonaceous group.

In WO 2011/089017 A1, a novel UHMWPE material is disclosed, comprising both Hf and Cr as a catalyst residue, preferably with the proviso that the Cr catalyst is not comprised in oxidic form in the polyethylene, displaying excellent abrasion resistance amongst other properties. The Hf and Cr, in the context of the invention, stems preferably from single site catalyst of the metallocene and/or half-sandwich metallocene type comprising organic, multidentate ligands (i.e. not from a Phillips catalyst).

WO 2010/139720 A1 pertains to a process for manufacturing a UHMWPE, wherein olefin monomers are contacted with a catalytic system under polymerisation conditions under formation of a polyethylene, wherein the catalytic system comprises an active component on a particulate carrier in a site density in the range of 5*10$^{-9}$ to 5*10$^{-6}$ mole of catalytic sites per m$^2$ of carrier surface area, the particulate carrier having an average particle diameter in the range of 1-300 nm, wherein the polyethylene has a Mw of at least 500 000 g/mol, and an elastic shear modulus $G^0_N$, determined directly after melting at 160° C. of at most 1.4 MPa.

Fujita et al. at Mitsui Chemicals Inc. disclosed a new class of catalysts for living olefin polymerisations, the so-called phenoxyimine-based (FI) catalysts (*Catalysis Today*, Volume 66, Issue 1, 15 Mar. 2001, Pages 63-73 and *Chemical Review*, 2011, 111, 2363-2449). M. S. Weiser et al. report in the *Journal of Organometallic Chemistry* 2006, 691, 2945-2952 tailoring such a phenoxyimine catalyst for the synthesis of UHMWPE, as well as atactic polypropylene. *Macromolecules* 2011, 44, 5558-5568, also discloses phenoxyimine catalysts to prepare disentangled UHMWPE namely at conditions of a) low polymerization temperature, so that the crystallization rate is faster than the polymerization rate, and b) low concentrations of active sites, so as to minimize the interaction of the growing chains.

However, a drawback of such phenoxyimine-based catalysts is that the phenoxy group does not provide sufficient rigidity to prevent the resulting metallic complex from adopting different conformations leading to the presence of multiple catalytic sites. Furthermore, phenoxy groups only have a limited number of sites which can bear substituents, these being needed for tailoring and fine-tuning in order to increase catalytic activity and/or enhance the control over the UHMWPE microstructure (short-chain branching, long-chain branching etc).

Thus a new family of single-site catalysts are needed, which have ligands which are more rigid, which are easier to fine-tune with a larger number of possible substituents but are also capable of preparing UHMWPE, preferably having a narrow molecular weight distribution Mw/Mn (also called polydispersity index) namely from 1 to 5, even more preferably 1 to 3.

Figure 1:
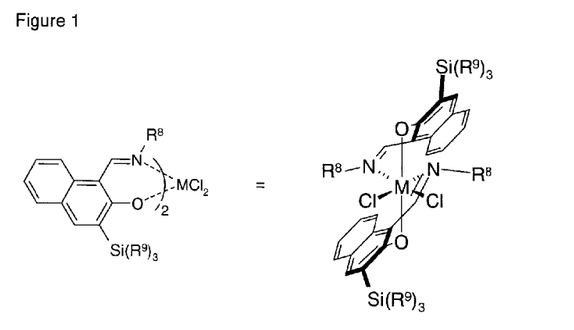
FIG. 1 shows a proposed three-dimensional structure of the naphthoxy-imine catalysts according to the invention.

The solution to this technical problem was found by providing Group 4 transition metal based catalysts having iminonaphthol ligands. The backbone of the iminonaphthol ligand is larger and completely planar because of the use of the aromatic naphthalene skeleton (FIG. 1). Moreover, without being bound by theory, this would lock the conformation of these complexes, unlike the phenoxyimine ligands of the prior art which are known to display flexible coordination modes. This gives opportunities for increased ligand fine-tuning and results in increased rigidity of group 4 transition metal complexes thus providing more precise control over the microstructure of polymers prepared by such catalysts. This broad family of ligands has already been disclosed in WO 2009/133026, but in the context of preparing vinyl-end capped ethylene oligomers using Group 6 metallic complexes only.

SUMMARY OF THE INVENTION

An objective of the invention is solved using a naphthoxy-imine Group 4 metal based catalyst.

In particular, the invention uses the following bidentate pro-ligand of formula (I) or its tautomeric form of formula (I')

wherein $R^1$, $R^3$, $R^4$, $R^5$, $R^6$ and $R^7$ are each independently selected from hydrogen, substituted or unsubstituted alkyl, cycloalkyl or aryl groups comprising from 1 to 12 carbon atoms, a halogen, or silyl groups, wherein two or more of said groups can be linked together to form one or more rings, wherein Q is an atom selected from Group 16, preferably from oxygen or sulphur, wherein A is an atom selected from Group 15, preferably from nitrogen or phosphorus, wherein $R^2$ is independently selected from an unsubstituted or substituted aryl or cycloalkyl group having from 1 to 12 carbon atoms, or from $Z(R^9)_3$ wherein Z is an atom selected from Group 14 of the Periodic Table, preferably from silicon or carbon, and each $R^9$ is independently selected from a substituted or unsubstituted aryl, alkyl or cycloalkyl group having from 1 to 12 carbon atoms, with the restriction that $R^2$ is a bulky group, at least as bulky as tert-butyl, wherein $R^8$ is an unsubstituted or substituted aryl, alkyl or cycloalkyl group having from 1 to 12 carbon atoms, wherein only A and Q are capable of chelating to a same metal M.

WO 2009/133026 discloses naphthoxy ligands in a broad sense, in particular for preparing Group 6 metal based catalysts, which are suitable for preparing vinyl-end capped oligomers of ethylene. However, only one bidentate ligand is specifically disclosed in WO2009/133026, namely in the examples, wherein R1 and R3 to R7 are hydrogens, $R^8$ is $C_6F_5$ and $R^2$ is $SiPh_3$. There is no disclosure in WO 2009/133026 of any use in a Group 4 based metal catalyst for olefin polymerisation, let alone to prepare polyethylene such as UHMWPE.

The invention covers a process for preparing such ligands.

Furthermore, the invention also covers a metallic complex of formula VII:

wherein $R^1$, $R^3$, $R^4$, $R^5$, $R^6$ and $R^7$ are each independently selected from hydrogen, alkyl, cycloalkyl or aryl group comprising from 1 to 12 carbon atoms, a halogen, or a silyl group, wherein two or more of said groups can be linked together to form one or more rings, wherein Q is an atom selected from Group 16, preferably from oxygen or sulphur, wherein A is an atom selected from Group 15, preferably from nitrogen or phosphorus, wherein $R^2$ is independently selected from an unsubstituted or substituted aryl or cycloalkyl group having from 1 to 12 carbon atoms, or from $Z(R^9)_3$ wherein Z is an atom selected from Group 14 of the Periodic Table, and each $R^9$ is independently selected from a hydrogen, substituted or unsubstituted aryl, alkyl or cycloalkyl group having from 1 to 12 carbon atoms, with the restriction that $R^2$ is a bulky group, at least as bulky as tert-butyl, wherein $R^8$ is an unsubstituted or substituted aryl, alkyl or cycloalkyl group having from 1 to 12 carbon atoms, and wherein M is a metal Group 4 of the Periodic Table, preferably selected from titanium, zirconium or hafnium, wherein each X is the same or different and is a halogen atom, preferably chlorine, fluorine or bromine, a substituted or unsubstituted alkyl, cycloalkyl or aryl group comprising from 1 to 12 carbon atoms, an amido group, or an alkoxide group.

The invention also covers the process for preparing such metallic complexes.

In addition, the invention covers the catalyst system comprising the metallic complex of the invention and an activating agent. Optionally, the catalyst system is supported.

The invention also covers the process for (co-)polymerising olefins, preferably ethylene, in the presence of the catalyst system of the invention and to the polyolefin thereby obtained. In particular, the process for preparing ultra high molecular weight polyethylene (UHMWPE) in the presence of the catalyst system of the invention is disclosed and the UHMWPE obtained thereby.

DETAILED DESCRIPTION

The Bidentate Pro-ligand

The bidentate pro-ligand is based on a naphthoxy-imine compound. These are more rigid than previously known phenoxy-imine compounds used in olefin polymerisation catalysts. The rigidity increases the activity of the catalyst and its lifetime, thereby allowing a 'living' polymerisation process to obtain polyolefins of higher molecular weight, particularly ultra high molecular weight polyethylene (UHMWPE). Furthermore, the number of possible substituents makes it possible to tailor and fine-tune the pro-ligand, in particular to increase activity and the molecular weight of the end polyolefin.

In particular, the invention uses the following bidentate pro-ligand of formula I or its tautomeric form of formula I' wherein only A and Q are capable of chelating to a same metal M.

$R^1$, $R^3$, $R^4$, $R^5$, $R^6$ and $R^7$ are each independently selected from hydrogen, substituted or unsubstituted alkyl, cycloalkyl or aryl groups comprising from 1 to 12 carbon atoms, a halogen, or silyl groups, wherein two or more of groups of $R^3$ to $R^7$ can be linked together to form one or more rings. Substituents, if present, can be selected from any aryl, alkyl, or cycloalkyl group having from 1 to 12 carbon atoms, silyl group or halogen. A silyl group can be selected from $SiR^*_3$ wherein each $R^*$ can be the same or different alkyl, cycloalkyl or aryl group having from 1 to 12 carbon atoms. By way of example, the silyl group can be selected from tri-methyl silyl ($SiMe_3$), tri-ethyl silyl ($SiEt_3$), tri-iso-propyl silyl ($Sii-Pr_3$) or from triphenyl silyl ($SiPh_3$).

In a particular embodiment, $R^1$, $R^3$, $R^4$, $R^5$, $R^6$ and $R^7$ are hydrogen.

Q is an atom selected from Group 16, preferably from oxygen or sulphur. Most preferably, Q is an oxygen atom.

A is an atom selected from Group 15, preferably from nitrogen or phosphorus. Most preferably, A is a nitrogen atom.

$R^2$ is a bulky group, sterically at least as big as tert-butyl. Bulkiness as used herein is based on the u values introduced by Charton (J. Am. Chem. Soc. 1975, 97, 1552), which values are derived from van der Waals radii. These values are discussed at page 411 of March's Advanced Organic Chemistry—Reactions, Mechanisms, and Structure (6th Edition, Wiley, 2007).

$R^2$ can be independently selected from an unsubstituted or substituted aryl or cycloalkyl group having from 1 to 12 carbon atoms. Preferably, in this embodiment $R^2$ is preferably selected from a phenyl group, a naphthyl group, a cyclohexyl group, an adamantyl group or a cumyl group. Substituents, if present, can be selected from any aryl, alkyl, or cycloalkyl group having from 1 to 12 carbon atoms, silyl group or halogen. A halogen is preferably selected from fluorine, chlorine and bromine, more preferably it is chlorine or fluorine, most preferably fluorine. A silyl group can be selected from $SiR^*_3$ wherein each $R^*$ can be the same or different alkyl, cycloalkyl or aryl group having from 1 to 12 carbon atoms. By way of example, the silyl group can be selected from tri-methyl silyl ($SiMe_3$), tri-ethyl silyl ($SiEt_3$), tri-iso-propyl silyl ($Sii-Pr_3$) or from triphenyl silyl ($SiPh_3$).

$R^2$ can also be alternatively selected from $Z(R^9)_3$ wherein Z is an atom selected from Group 14 of the Periodic Table, preferably from silicon or carbon, and each $R^9$ can be the same or different and is independently selected from a substituted or unsubstituted aryl, alkyl or cycloalkyl group having from 1 to 12 carbon atoms, with the restriction that $R^2$ is a bulky group, sterically at least as big as tert-butyl. Substituents, if present, can be selected from any aryl, alkyl, or cycloalkyl group having from 1 to 12 carbon atoms, silyl group or halogen. A halogen is preferably selected from fluorine, chlorine and bromine, more preferably it is chlorine or fluorine, most preferably fluorine. A silyl group can be selected from $SiR^*_3$ wherein each $R^*$ can be the same or different alkyl, cycloalkyl or aryl group having from 1 to 12 carbon atoms. By way of example, the silyl group can be selected from tri-methyl silyl ($SiMe_3$), tri-ethyl silyl ($SiEt_3$), tri-iso-propyl silyl ($Sii-Pr_3$) or from triphenyl silyl ($SiPh_3$).

In one embodiment, $R^2$ is an alkyl based $Z(R^9)_3$ group, wherein Z is a carbon atom. Each $R^9$ can be the same or different. In one embodiment, all $R^9$ are preferably the same and are selected from methyl, ethyl, i-propyl, n-propyl, n-butyl, i-butyl, tert-butyl, pentyl groups, hexyl groups, cyclohexyl ($C_6H_{11}$), phenyl (Ph). Most preferably $R^2$ is thus tert-butyl ($C(CH_3)_3$) or triphenylmethyl ($CPh_3$).

In another preferred embodiment, $R^2$ is a silyl group Z$(R^9)_3$, wherein Z is a silicon atom. Silicon is preferred since this provides additional rigidity and tolerance to the catalyst system.

Each $R^9$ can be the same or different. In one embodiment, all $R^9$ are preferably the same and are selected from methyl, ethyl, iso-propyl, n-propyl, n-butyl, iso-butyl, tert-butyl, pentyl groups, hexyl groups, cyclohexyl ($C_6$—$H_{11}$), phenyl (Ph) etc. Thus preferably $Z(R^9)_3$ is thus selected from $SiMe_3$, $SiEt_3$, $Sii$-$Pr_3$ or $SiPh_3$.

Most preferably, $R^2$ is selected from $SiMe_3$ or $SiPh_3$.

$R^8$ is an unsubstituted or substituted aryl, alkyl or cycloalkyl group having from 1 to 12 carbon atoms. Substituents, if present, can be selected from any aryl, alkyl, or cycloalkyl group having from 1 to 12 carbon atoms, silyl group or halogen. A halogen is preferably selected from fluorine, chlorine or bromine atom, more preferably it is chlorine or fluorine, most preferably fluorine. A silyl group can be selected from $SiR*_3$ wherein each R* can be the same or different alkyl, cycloalkyl or aryl group having from 1 to 12 carbon atoms. By way of example, the silyl group can be selected from tri-methyl silyl ($SiMe_3$), tri-ethyl silyl ($SiEt_3$), tri-iso-propyl silyl ($Sii$-$Pr_3$) or from triphenyl silyl ($SiPh_3$).

In a preferred embodiment, $R^8$ is selected from an unsubstituted phenyl, naphthyl or a cyclohexyl group. Preferably, these are unsubstituted. In a more preferred embodiment $R^8$ is a cyclohexyl group ($C_6H_{11}$):

In another preferred embodiment, $R^8$ is a fully substituted phenyl, naphthyl or cyclohexyl group, preferably fully substituted with a halogen, most preferably with fluorine. In a more preferred embodiment $R^8$ is a pentafluorophenyl group ($C_6F_5$):

Preferred embodiments of the pro-ligand according to the invention are:

More preferably:

or or or

Even more preferably:

Or:

Or:

Bidentate Pro-ligand Synthesis

The invention covers the process for preparing some of the pro-ligands useful in the invention, wherein A is nitrogen and Q is oxygen. Preferably, the process for preparing the bidentate pro-ligand wherein A is nitrogen and Q is oxygen comprises the following steps of:

a) providing a 2-methoxynaphthalene of formula II:

(II)

$R^3$, $R^4$, $R^5$, $R^6$ and $R^7$ being defined as above b) reacting formula II with $R^2X'$, wherein X' is a leaving group in the presence of a base, preferably sec-BuLi. When $R^2$ is a silyl-based group, X' is preferably a halogen. When $R^2$ is a carbonaceous group (substituted or unsubstituted alkyl, cycloalkyl or aryl group), X' is preferably a halogen, mesylate or tosylate. The compound of formula III is obtained:

(III)

c) reacting formula III with an electrophilic bromine source, such as N-bromosuccinimide or bromine $Br_2$, to obtained a compound of formula IV:

(IV)

d) reacting formula IV with acylchloride $R^1COCl$ in the presence of a base, preferably tert-BuLi, to obtain a compound of formula V':

(V')

wherein $R^1$ is an unsubstituted or substituted aryl, alkyl, or cycloalkyl group comprising from 1 to 12 carbon atoms, a halogen, or a silyl group (i.e. to form a ketone group);

e) deprotecting the compound of formula (V) or (V') obtained in step d), preferably by treatment with $BBr_3$, in order to obtain a compound of formula VI:

(VI)

Preferably, compound of formula (V) or (V') obtained in step d) is purified before deprotection of the alcohol group of step e). This can be carried out by chromatographic purification.

f) condensation of the compound of formula VI with an amine $R^8$—$NH_2$ (also known as Schiff-base condensation) in the presence of catalytic amounts of an acid, such as formic acid (HCOOH), acetic acid ($CH_3COOH$), sulphuric acid ($H_2SO_4$), or p-Toluenesulfonic acid (PTSA), optionally in the presence of tetraethyl orthosilicate or titanium tetrachloride, to obtain compounds of formula I and its tautomeric form I', wherein A is nitrogen and Q is oxygen. The amine is preferably selected from ($C_6F_5$—$NH_2$) pentafluoroaniline or cyclohexylamine ($C_6H_{11}$—$NH_2$). This step is preferably carried out in a solvent under reflux conditions.

(I)        (I')

Figure 2:
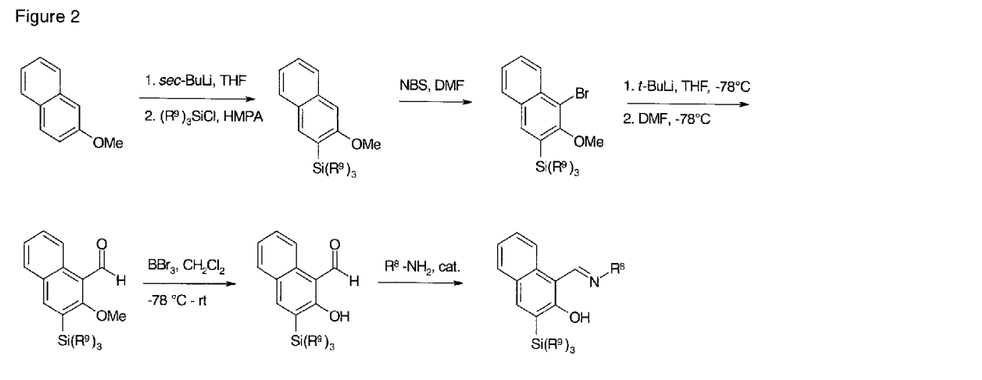
FIG. 2 shows a scheme for the preparation of the bidentate pro-ligand according to the invention.

An overview of the synthesis of the ligands wherein $R^1$, $R^3$, $R^4$, $R^5$, $R^6$, $R^7$=H, $R^2$=$SiR^9_3$ and $R^8$= are shown in FIG. 2.

Metallic Complex

Furthermore, the invention also covers a metallic complex of formula VII:

(VII)

The metallic complex according to the invention can be prepared by the complexation reaction of the corresponding bidentate pro-ligand of Formula (I) or (I') in the presence of a base, preferably n-BuLi:

$R^1$, $R^3$, $R^4$, $R^5$, $R^6$, $R^7$ and $R^8$ and A and Q have the same definitions as above for the bidentate pro-ligand, $R^1$, $R^3$, $R^4$, $R^5$, $R^6$, $R^7$ and $R^8$ and A and Q have the same definitions as above for the bidentate pro-ligand. However, the following metallic complex of formula (VIII) is expressly included:

(VIII)

M is a metal Group 4 of the Periodic Table, preferably selected from titanium, zirconium or hafnium. More preferably M is selected from titanium or zirconium. Most preferably, M is titanium.

X is the same or different and is selected from a halogen atom, substituted or unsubstituted alkyl, cycloalkyl or aryl group comprising from 1 to 12 carbon atoms, an amido group, or an alkoxide group. More preferably X is a halogen atom, preferably selected from chlorine, fluorine or bromine. Most preferably, both X are chlorine atoms.

Thus, most preferably, the complex is a titanium(IV) chloride complex or a zirconium (IV) dichloride complex. Most preferably, the complex is a titanium(IV) dichloride complex.

being expressly included.

The complexation reaction takes place with the bidentate pro-ligand in the presence of the base with a metallic salt $MX_4$ wherein M and X are defined as above. Preferably, the bidentate pro-ligand is suspended/dissolved in a solvent/diluent such as an ether, preferably diethylether or tetrahydrofurane (THF). Preferably, the metallic salt $MX_4$ is added as a solution, such as an alkane, for instance pentane, when M is titanium. Preferably, the metallic salt $MX_4$ is added as a solid, when M is zirconium.

Two moles of the bidentate pro-ligand are used per mole of metallic salt. When using n-BuLi as the base, two molar equivalents of n-BuLi are used.

The complexation reaction is preferably carried out at a temperature of from −80° C. to 25° C., preferably around −80° C. to −70° C., for a period of 1 to 24 hours. For titanium complexes lower temperatures than for zirconium complexes are preferred.

Catalyst System

In addition to the above, the invention covers the catalyst system comprising the metallic complex of the invention and an activating agent The present invention also discloses a catalyst system comprising the Group 4 metallic complex of formula VII and an activating agent having an alkylating/ionising action. Suitable activating agents are well known in the art. Examples include aluminium alkyls, alumoxanes, preferably MAO, and boron-containing compounds e.g. perfluoroborate.

The activating agent can be an aluminium alkyl represented by formula $AIR*nX_{3-n}$ wherein R* is an alkyl having from 1 to 20 carbon atoms and X is a halogen. The preferred aluminium alkyls are triisobutylaluminium (TIBAL) or triethylaluminium (TEAL). These can be used in combination with a perfluoroborate e.g. $[Ph_3C][B(C_6F_5)_4]$ or $[Me_2NPhH][B(C_6F_5)_4]$, which can be used to increase the molecular weight of the produced polyolefin. For example, using a combination of [Ph$_3$C][B(C$_6$F$_5$)$_4$]/TIBAL or of [Me$_2$NPhH][B(C$_6$F$_5$)$_4$]/TIBAL.

Alternatively, it can be aluminoxane and comprise oligomeric linear and/or cyclic alkyl aluminoxanes represented by formula for oligomeric, linear aluminoxanes and by formula for oligomeric, cyclic aluminoxane, wherein n is 1-40, preferably 1-20, m is 3-40, preferably 3-20 and R* is a C$_1$-C$_8$ alkyl group and preferably methyl or isobutyl.

Preferably, the activating agent is selected from methylaluminoxane (MAO) and ethylaluminoxane. More preferably the activating agent is MAO.

The amount of activating agent is selected to give an Al/M ratio of from 100 to 10000, preferably of 200 to 4000, more preferably from 500 to 3000, most preferably from to 1000 to 5000. The amount of activating agent depends upon its nature.

Suitable boron-containing agents may also be used for activating the metallic complex to form a catalyst system. These include for example a triphenylcarbenium boronate such as tetrakis(pentafluorophenyl)borato-triphenylcarbenium as described in EP-A-0427696, or those of the general formula [L'-H]+[B Ar1 Ar2X3X4]- as described in EP-A-0277004 (page 6, line 30 to page 7, line 7).

The amount of boron-containing activating agent is selected to give a B/M ratio of from 0.5 to 5, preferably of about 1.

The catalyst system may comprise an optional scavenger that may be selected from triethylaluminium, triisobutylaluminum, tris-n-octylaluminium, tetraisobutyldialuminoxane, diethylzinc, tris-n-hexyl aluminum or diethylchloroaluminum. Usually, the scavenger is added after activation of the catalyst with the activating agent.

In another preferred embodiment, according to the present invention, the metallic complex of formula VII may be deposited on a conventional inorganic support.

In one embodiment, the support comprises silica and/or alumina, preferably from 10 to 100 wt % of silica and/or preferably from 10 to 100 wt % of alumina. Alternatively, the support may also be an activating support such as fluorinated alumina silica. Preferably, the support is preimpregnated with MAO before adding the metallic complex. In another alternative, the support may comprise magnesium salt, preferably MgCl$_2$. Preferably, the support comprises from 10 to 100 wt % of magnesium salt.

Polymerisation Process and the Polyolefin

The invention also covers the process for (co-)polymerising olefins in the presence of the catalyst system of the invention. The process comprises the steps of:
a) injecting the catalyst system of the invention into the reactor;
b) injecting the olefins either before or after or simultaneously with step a);
c) maintaining the reactor under polymerisation conditions;
d) retrieving the polyolefin.

The olefin is preferably ethylene to obtain a polyethylene in step d) comprising at least 50% wt of ethylene moieties.

This polymerisation can occur in the presence of one or more comonomers selected from an alpha-olefin comprising from 1 to 12 carbon atoms, preferably propylene or 1-hexene, to retrieve an ethylene copolymer in step d). Optionally hydrogen can be added to control the molecular weight of the polyethylene.

The polymerisation process can be carried out in solution, in a slurry or in the gas phase. In a slurry process, the catalyst system is preferably supported. The slurry process can be carried out in reactor(s) suitable for such processes, namely, continuously stirred tank reactors (CSTRs) or slurry loop reactors (in particular liquid full loop reactors). The pressure in the reactor can vary from 0.5 to 50 bars, preferably 5 to 25 bars, most preferably around 20 bar. The polymerisation temperature can vary from 0 to 100° C., preferably from 25 to 85° C.

In particular, the catalyst system of the invention is particularly suitable for preparing UHMWPE from ethylene. UHMWPE is herein defined as a substantially linear ethylene homopolymer or copolymer with a weight average molecular weight of at least 1,000,000 g/mol (Da), as obtained from intrinsic viscosity ($\eta$) measurements using Margolies' equation: $M_v = 5.37 \times 10^4 (\eta)^{1.37}$, wherein $M_v$ is defined as the viscosimetric molecular weight average.

Preferably the UHMWPE has an intrinsic viscosity of at least 7.5 dL/g measured according to ASTM D2857, more preferably at least 8.0 dL/g, most preferably at least 10. dL/g.

UHMWPE can be obtained with the present catalyst in the slurry or solution phase, using a heterogeneous (supported) catalyst system in the former case and a homogeneous (unsupported) catalyst system in the latter. The diluent or solvent of choice is a hydrocarbon, preferably a saturated hydrocarbon having from 4 to 12 carbon atoms, such as isobutane or hexane. In a specific embodiment the hydrocarbon diluent or solvent may be toluene.

Due to the metallic complex being a single-site catalyst, the UHMWPE has a polydispersity index (molecular weight distribution Mw/Mn) from 1 to 5, preferably 1 to 4, more preferably from 1 to 3, most preferably from 1 to 2.

In order to prepare UHMWPE, the polymerisation temperature is preferably kept as low as possible, from 40 to 90° C., more preferably around 50 to 80° C., most preferably around 60° C. The polymerisation is carried out under a pressure of about 5 to 25 bars, and under the complete absence of hydrogen gas. Preferably, the catalyst concentration is sufficiently for retrieving ultra high molecular weight polyethylene. More preferably the catalyst concentration in the diluent/solvent is less than 0.05 mM, most preferably less than 0.03 mM.

To obtain disentangled UHMWPE as described by Rastogi et al. in *Macromolecules* 2011, 44, 5558-5568, the polymerisation process can be carried out in a solution process using the catalyst system homogeneously (i.e. non-supported) at a low temperature from around 0° C. to 10° C., preferably around 5° C. and at extremely low concentration of catalyst (preferably less than 0.01 mM). In this way, the polymerisation temperature is low enough such that the crystallisation rate is faster than the polymerisation rate. The low concentration of active site also results in a minimization of the interaction between growing chains. The advantage of disentangled UHMWPE is the higher modulus and strength of films and fibres made therefrom. In addition, the disentangled UHMWPE can be stretched biaxially which is difficult, even impossible, with entangled UHMWPE.

The UHMWPE (both entangled and disentangled) obtained using the catalyst system of the invention can be transformed using inter alia some of the following processes: compression molding, ram extrusion, gel spinning, and sintering. The UHMWPE are used to prepare films, tapes, and fibres for biomedical devices, ballistic protection and ropes for nautical purposes (e.g. fishing and sailing), pressure pipes, large-part blow moulding, extruded sheets etc. These techniques are well-known in the polymer industry.

EXAMPLES

General Procedures. All reactions were carried out under an atmosphere of nitrogen using standard Schlenk techniques or in a glovebox. With exception of the compounds given below, all reagents were purchased from commercial suppliers and used without further purification. THF, diethyl ether and toluene were distilled from sodium benzophenone ketyl; CH2Cl2, isopropanol, and pentane were distilled from CaH2 under nitrogen.

Example 1

Ti-based Catalytic Polymerisation to Obtain UHMWPE

Ligand Synthesis

Bidentate iminonaphthol (NI) ligands:

abbreviated as $NI(SiR^9{}_3-R^8)$ wherein NI represents naphthoxyimine, were synthesized with the yields presented below. The synthesis was carried out according to the scheme provided in FIG. 2, in analogy with the scheme provided in WO2009/133026, which describes in particular the synthesis of such ligands starting from 2-methoxynaphthalene, wherein in the final product $R^2$ was $SiPh_3$ and $R^8$ is either an alpha-quinoleine, a $CH_2$-(2-pyridyl) or $C_6F_5$ group. The corresponding procedures were used to obtain the new NI-ligands having $SiMe_3$ as $R^2$ and/or $C_6H_{11}$ as $R^8$.

Ligand A: $NI(SiMe_3-C_6-H_{11})$ 82%

Ligand B: $NI(SiMe_3-C_6F_5)$ 84%

Ligand C: $NI(SiPh_3-C_6F_5)$ 77%

Before deprotection of the alcohol (step e as claimed), the product of step d) (compound of formula V as claimed), was purified by chromatographic purification to isolate the intermediate protected alcohol before deprotection.

The final step in the synthesis was the Schiff-base condensation reaction of the napthoxyaldehydes with and amine, namely either pentafluoroaniline or cyclohexylamine to obtain the ligands wherein $R^8=C_6F_5$ and $R^8=C_6H_{11}$ respectively. In the former case para-toluenesulfonic acid was used as a catalyst in refluxing toluene under azeotropic water-removal whereas for the alkylamine provided the products in refluxing methanol without the need of a catalyst. Thus three different $NI(SiR^9_3-R^8)$ ligands were successfully synthesized in 77-84% yield.

Metallic Complex Synthesis

Figure 3:
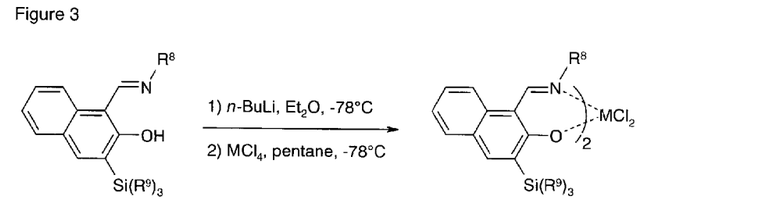
FIG. 3 shows a scheme for the preparation of the metallic complex according to the invention.

Metal complexation of the naphthoxy-imine ligands was investigated with titanium (FIG. 3). Deprotonation of the ligand with n-butyllithium followed by reaction with half an equivalent of the corresponding tetrachloro metal-precursors gave rise to the formation of $(NI)_2TiCl_2$ Complexes A, B and C in moderate to good yield.

Synthesis of $[\{NI(SiR^9_3-R^8)\}_2TiCl_2]$ Complexes A, B and C. n-Butyllithium (2 eq.) was added dropwise to the corresponding iminonaphthol Ligands A, B and C (2 eq.) in diethylether at −78° C. and stirred for 2 h allowing to warm to room temperature. The reaction mixture was cooled to −78° C., and a solution of $TiCl_4$ (1 eq.) in pentane was added dropwise. The resulting suspension was stirred overnight allowing warming to room temperature. Solvents were removed in vacuo and the residue was dissolved in dichloromethane. LiCl was removed by centrifugation and the solvent was removed in vacuo. The resulting brown-red solids were washed with a minimal amount of pentane.

The following analytical results were obtained:

Complex A [{NI(SiMe$_3$-C$_6$H$_{11}$)}$_2$TiCl$_2$] Yield: 580 mg (98%). $^1$H-NMR (500 MHz, CD$_2$Cl$_2$): δ/ppm 0.62 (s, SiMe$_3$, 9H), 0.86-2.22 (m, CH$_2$ cyclohexyl, 10H), 3.93 (m, CH cyclohexyl, 1H), 7.45 (t, J=7.5 Hz, Nph, 1H), 7.59 (t, J=7.5 Hz, Nph, 1H), 7.89 (d, J=7.5 Hz, Nph, 1H), 7.96 (d, J=7.5 Hz, Nph, 1H), 8.20 (s, Nph, 1H), 9.00 (s, CH imine, 1H). $^{13}$C-NMR (125 MHz, CD$_2$Cl$_2$): δ/ppm 1.3 (SiMe$_3$), 16.2, 25.0, 27.6, 27.9, 29.2, 33.9, 36.5, 36.9, 37.4, 67.8, 118.9, 122.0, 126.9, 130.9, 131.5, 133.2, 136.1, 146.2, 160.5, 167.9.

Complex B [{NI(SiMe$_3$-C$_6$F$_5$)}$_2$TiCl$_2$] Yield: 288 mg (40%). $^1$H-NMR (500 MHz, CD$_2$Cl$_2$): δ/ppm 0.42 (s, SiMe$_3$, 9H), 7.54 (t, J=5.5 Hz, Nph, 1H), 7.65 (t, J=5.0 Hz, Nph, 1H), 7.91 (vt, J=8.5 Hz, Nph, 2H), 8.28 (s, Nph, 1H), 9.01 (s, CH imine, 1H). $^{13}$C-NMR (125 MHz, CD$_2$Cl$_2$): δ/ppm −1.2 (SiMe$_3$), 115.5, 119.6, 126.0, 129.4, 130.2, 130.3, 131.2, 134.24, 167.9, 170.0.

Complex C [{NI(SiPh$_3$-C$_6$F$_5$)}$_2$TiCl$_2$] Yield: 390 mg (71%). $^1$H-NMR (500 MHz, CD$_2$Cl$_2$): δ/ppm 7.05-7.96 (m, SiPh3+Nph, 20H), 9.27 (s, CH imine, 1H).

Complex X (outside the invention) [{FI(siph$_3$-C$_6$F$_5$)}$_2$ticl$_2$] wherein FI represents phenoxyimine.

Preparation of Ultra High Molecular Weight Polyethylene

The potential of NI-catalysts of complexes A, B and C in the presence of MAO cocatalyst for the preparation of UHM-WPE was evaluated in a parallel reactor under conditions that favour high molecular weight (20 bar C2, 60° C., absence of H$_2$). The results are depicted in Table 1 below. Intrinsic viscosity measurements have been used to determine the molecular weight of the resins produced according to ASTM D2857.

Reactions were run both in hexane as well as toluene to study the solvent effect. For NI catalysts of complexes A, B and C activities in hexane are higher by about 20-50%. Also the molecular weight is generally higher in hexane; therefore, saturated hydrocarbons seem to be the solvent of choice for high activity and molecular weight with these catalysts.

The concentration of the catalyst plays an important role in the polymerisation process to obtain UHMWPE in particular, which is in line with the living polymerization character of these catalysts, since the concentration of the catalyst had to be kept below 1 µmol in order to obtain an intrinsic viscosity of above 7.5 dL/g (see Entry 5 below which used a higher concentration of catalyst).

The catalyst substituents also play a role in fine-tuning the catalytic properties. NI complexes B and C containing a $C_6F_5$ group provide the highest molecular weights. Such an effect can be tentatively explained by a C—F interaction between the growing chain and the ligand thus prohibiting beta-elimination. The size of the $SiR_3$ substituent leads to slightly higher molecular weights when going from $SiMe_3$ to $SiPh_3$ (entries 3 and 6).

For comparative purposes, it is believed that the use of complex X in the conditions stated in Table 1 will result in the formation of a polyethylene with an intrinsic viscosity lower than 7.5 dL/g.

TABLE 1

Ethylene polymerization using NI titanium complexes A, B and C in a parallel reactor.[a]

| Entry | Catalyst Ti Complex | Catalyst amount (µmol) | Solvent | Yield (g) | Activity (kg PE/ mmol Ti × h) | Intrinsic Viscosity (dL/g) | $M_v$[b] (kDa) |
|---|---|---|---|---|---|---|---|
| 1 | A | 0.64 | Hexane | 0.77 | 1.19 ± 0.27 | 11.0 | 1913 |
| 2 | A | 0.64 | Toluene | 0.51 | 0.79 ± 0.06 | 7.7 | 1124 |
| 3 | B | 0.72 | Hexane | 1.34 | 1.84 ± 0.13 | 11.6 | 2070 |
| 4 | B | 0.72 | Toluene | 1.01 | 1.40 ± 0.07 | 14.2 | 2798 |
| 5 | C | 1.15 | Hexane | 1.25 | 1.09 ± 0.15 | 2.8 | 249 |
| 6 | C | 0.68 | Hexane | 0.73 | 1.07 ± 0.17 | 15.9 | 3312 |
| 7 | C | 0.68 | Toluene | 0.46 | 0.68 ± 0.02 | 8.6 | 1326 |
| 8 | X | 0.68 | Hexane | n.d. | n.d. | <7.5 | n.d. |

[a]Conditions: 20 bar $C_2H_4$, 1000 rpm, 60 min, 20 mL solvent, MAO 30% Al/M = 2000. Activities are averages of three or four runs.
[b]Viscosimetric molecular weight average Mv obtained from intrinsic viscosity using Margolies' equation.
n.d.: not determined The molecular weight distribution Mw/Mn measured by GPC or melt-state rheometry (RDA) is between 1 and 5 due to the single-site nature of the catalyst system.

When the performance of the newly developed NI catalysts is compared to other single site catalysts providing UHM-WPE (as disclosed for example in Jones Jr. et al. *Inorg. Chim. Acta* 2010, 364, 275-281 and by Fujita et al. *Adv. Synth. Catal.* 2002, 344, 477-493) the results are promising. With regards to the previously known phenoxy-imine catalysts, even further fine-tuning can now be carried out to optimize catalyst activity and obtain higher molecular weights. Due to the modular synthesis of naphthoxy-imine titanium catalysts and large number of possibilities to substitute the naphthyl skeleton, such fine-tuning would be both facile and likely to yield improved systems.

Example 2

Zr-based Catalytic Polymerisation to Obtain PE

Experiments were also carried out to prepare polyethylene from zirconium-based catalyst systems according to the invention.

Ligand Synthesis

The same procedures as described for Example 1 were used.

In addition to Ligand C, a further ligand was synthesized.

Ligand D: NI($SiPh_3$-$C_6H_{11}$) at 91% yield:

-continued

Metallic Complex Synthesis

Synthesis of [{NI($SiR_3$—Ar)}$_2ZrCl_2$] complexes 5-6. n-Butyllithium (2 eq.) was added dropwise to the corresponding iminonaphthol ligand C or D (2 eq.) in diethylether at −78° C. and stirred for 2 h allowing to warm to rt. The solvent was removed in vacuo and the residue was suspended in pentane. $ZrCl_4$ (1 eq.) was added and the suspension was stirred overnight at room temperature. The resulting yellow suspension was filtered and the residue was washed with pentane and dissolved in dichloromethane. LiCl was removed by centrifugation and the solvent was removed in vacuo to obtain the product as a yellow solid.

The following Metallic Zr complexes D and E were prepared with Ligands C and D respectively:

Complex D [{NI($SiPh_3$-$C_6F_5$)}$_2ZrCl_2$] Yield: 462 mg (80%). The zirconium complexes gave $^1H$ and $^{13}C$ NMR spectra that were qualitatively identical to the corresponding titanium complexes, however, some line-broadening was observed indicating a more flexible coordination of the ligand.

Complex E [{NI(SiPh$_3$-C$_6$H$_{11}$)}$_2$ZrCl$_2$] Yield: 278 mg (49%).

Preparation of Polyethylene

The potential of NI-catalysts of Zr complexes D and E in the presence of MAO cocatalyst for the preparation of PE was evaluated in a parallel reactor under conditions of 20 bar C2, 60° C. in the absence of H$_2$. The results are depicted in Table 2 below. Intrinsic viscosity measurements have been used as above to determine the molecular weight of the resins produced according to ASTM D2857.

The concentration of the catalyst was added at a concentration of above 1 μmol in order to obtain an intrinsic viscosity of less than 7.5 dL/g. As described above, lower catalyst concentrations favour the preparation of UHMWPE, which was not envisaged herein.

The molecular weight distribution Mw/Mn measured by GPC is between 1 and 5 due to the single-site nature of the catalyst system.

CONCLUSION OF EXAMPLES

It has been shown that the catalysts system of the invention is suitable for preparing polyethylene and in particular ultra high molecular weight polyethylene.

The invention claimed is:

1. A metallic complex of formula VII (VII)

wherein $R^1$, $R^3$, $R^4$, $R^5$, $R^6$ and $R^7$ are each independently selected from hydrogen, alkyl, cycloalkyl or aryl group comprising from 1 to 12 carbon atoms, a halogen, or a silyl group, wherein two or more of said groups can be linked together to form one or more rings;

wherein Q is an atom selected from Group 16;

wherein A is an atom selected from Group 15;

wherein $R^2$ is independently selected from an unsubstituted or substituted aryl or cycloalkyl group having from 1 to 12 carbon atoms, or from $Z(R^9)_3$ wherein Z is an atom selected from Group 14 of the Periodic Table and each $R^9$ is independently selected from a hydrogen, substituted or unsubstituted aryl, alkyl or cycloalkyl group having from 1 to 12 carbon atoms, with the restriction that $R^2$ is a bulky group, at least as sterically bulky as tert-butyl;

wherein $R^8$ is an unsubstituted or substituted aryl, alkyl or cycloalkyl group having from 1 to 12 carbon atoms;

wherein M is a metal Group 4 of the Periodic Table; and wherein each X is the same or different and is a halogen atom, a substituted or unsubstituted alkyl, cycloalkyl or aryl group comprising from 1 to 12 carbon atoms, an amido group, or an alkoxide group.

2. The metallic complex of claim 1, wherein both X are chlorine, fluorine or bromine.

TABLE 2

Ethylene polymerization using NI zirconium complexes D and E in a parallel reactor.[a]

| Entry | Catalyst Zr Complex | Catalyst amount (μmol) | Solvent | Yield (g) | Activity (kg PE/ mmol Zr × h) | Intrinsic Viscosity (dL/g) | $M_v$[b] (kDa) |
|---|---|---|---|---|---|---|---|
| 8 | D | 1.02 | Hexane | 1.34 | 1.31 ± 0.49 | 1.7 | 118 |
| 9 | E | 1.38 | Hexane | 1.52 | 1.10 ± 0.09 | 2.4 | 198 |

[a]Conditions: 20 bar C$_2$H$_4$, 1000 rpm, 60 min, 20 mL solvent, MAO 30% Al/M = 2000. Activities are averages of three or four runs.
[b]Viscosimetric molecular weight average obtained from intrinsic viscosity using Margolies' equation.

3. The metallic complex of claim 1, wherein both X are chlorine.

4. The metallic complex of claim 1, wherein M is titanium, zirconium or hafnium.

5. The metallic complex of claim 1, wherein Q is oxygen or sulphur.

6. The metallic complex of claim 1, wherein A is nitrogen or phosphorus.

7. The metallic complex of claim 1, wherein Z is carbon or silicon.

8. A process for preparing the metallic complex of claim 1 by complexation reaction of a bidentate pro-ligand of formula (I) or (I') with a metallic salt $MX_4$ in the presence of a base:

wherein $R^1$, $R^3$, $R^4$, $R^5$, $R^6$ and $R^7$ are each independently selected from hydrogen, alkyl, cycloalkyl or aryl group comprising from 1 to 12 carbon atoms, a halogen, or a silyl group, wherein two or more of said groups can be linked together to form one or more rings;

wherein Q is an atom selected from Group 16;

wherein A is an atom selected from Group 15;

wherein $R^2$ is independently selected from an unsubstituted or substituted aryl or cycloalkyl group having from 3 to 12 carbon atoms, or from $Z(R^9)_3$ wherein Z is an atom selected from Group 14 of the Periodic Table, and each $R^9$ is independently selected from a hydrogen, substituted or unsubstituted aryl, alkyl or cycloalkyl group having from 1 to 12 carbon atoms, with the restriction that $R^2$ is at least as sterically bulky as tert-butyl;

wherein $R^8$ is an unsubstituted or substituted aryl, alkyl or cycloalkyl group having from 1 to 12 carbon atoms;

wherein M is a metal Group 4 of the Periodic Table;

wherein each X is the same or different and is a halogen atom selected from chlorine, fluorine or bromine; a substituted or unsubstituted alkyl, cycloalkyl or aryl group comprising from 1 to 12 carbon atoms; an amido group; or an alkoxide group.

9. The process of claim 8, wherein the base is n-BuLi.

10. The process of claim 8, wherein Q is oxygen or sulphur.

11. The process of claim 8, wherein A is nitrogen or phosphorus.

12. The process of claim 8, wherein M is titanium, zirconium or hafnium.

13. A catalyst system comprising the metallic complex of claim 1 and an activating agent selected from aluminium alkyl, boron containing compounds, or aluminoxane.

14. The catalyst system of claim 13, wherein the activating agent is methylaluminoxane (MAO).

15. The catalyst system of claim 13, wherein the catalyst system is supported on an inorganic support.

16. The catalyst system of claim 15, wherein the inorganic support comprises silica.

17. The catalyst system of claim 13, wherein the catalyst system is supported on a magnesium salt support.

18. The catalyst system of claim 17, wherein the magnesium salt support comprises $MgCl_2$.

19. A process for preparing polyolefins by polymerising olefins, and optionally comonomers, the process comprising:
injecting the catalyst system of claim 13 into a reactor;
injecting olefin monomer either before, after, or simultaneously with step a);
maintaining the reactor under polymerisation conditions;
retrieving the polyolefin.

20. The process of claim 19, wherein the olefin monomers comprises ethylene and one or more comonomers that are alpha-olefins comprising from 1 to 12 carbon atoms to retrieve polyethylene in step d).

21. The process of claim 20, wherein the one or more comonomers are propylene or 1-hexene.

22. The process of claim 20, wherein the catalyst concentration is sufficiently low to retrieve an ultra high molecular weight polyethylene having an intrinsic viscosity of at least 7.5 dL/g measured according to ASTM D2857.

* * * * *